US00PP18564P3

(12) United States Plant Patent
Meilland

(10) Patent No.: US PP18,564 P3
(45) Date of Patent: Mar. 4, 2008

(54) CLIMBING ROSE PLANT NAMED 'MEIGRAPPO'

(50) Latin Name: *Rosa hybrida*
Varietal Denomination: cv. Meigrappo

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 4 days.

(21) Appl. No.: 11/471,623

(22) Filed: Jun. 21, 2006

(65) Prior Publication Data

US 2007/0300333 P1 Dec. 27, 2007

(51) Int. Cl.
*A01J 5/00* (2006.01)

(52) U.S. Cl. ..... Plt./115

(58) Field of Classification Search ..... Plt./115
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct climbing rose plant is provided which abundantly forms on a nearly continuous basis attractive elegant blossoms that are red in coloration. Vigorous dense dark green foliage semi-glossy foliage is displayed that contrasts well with the red blossom coloration. Good tolerance to Black Spot and Oidium has been observed. The plant is well suited for providing attractive ornamentation in the landscape.

1 Drawing Sheet

Figure 1:
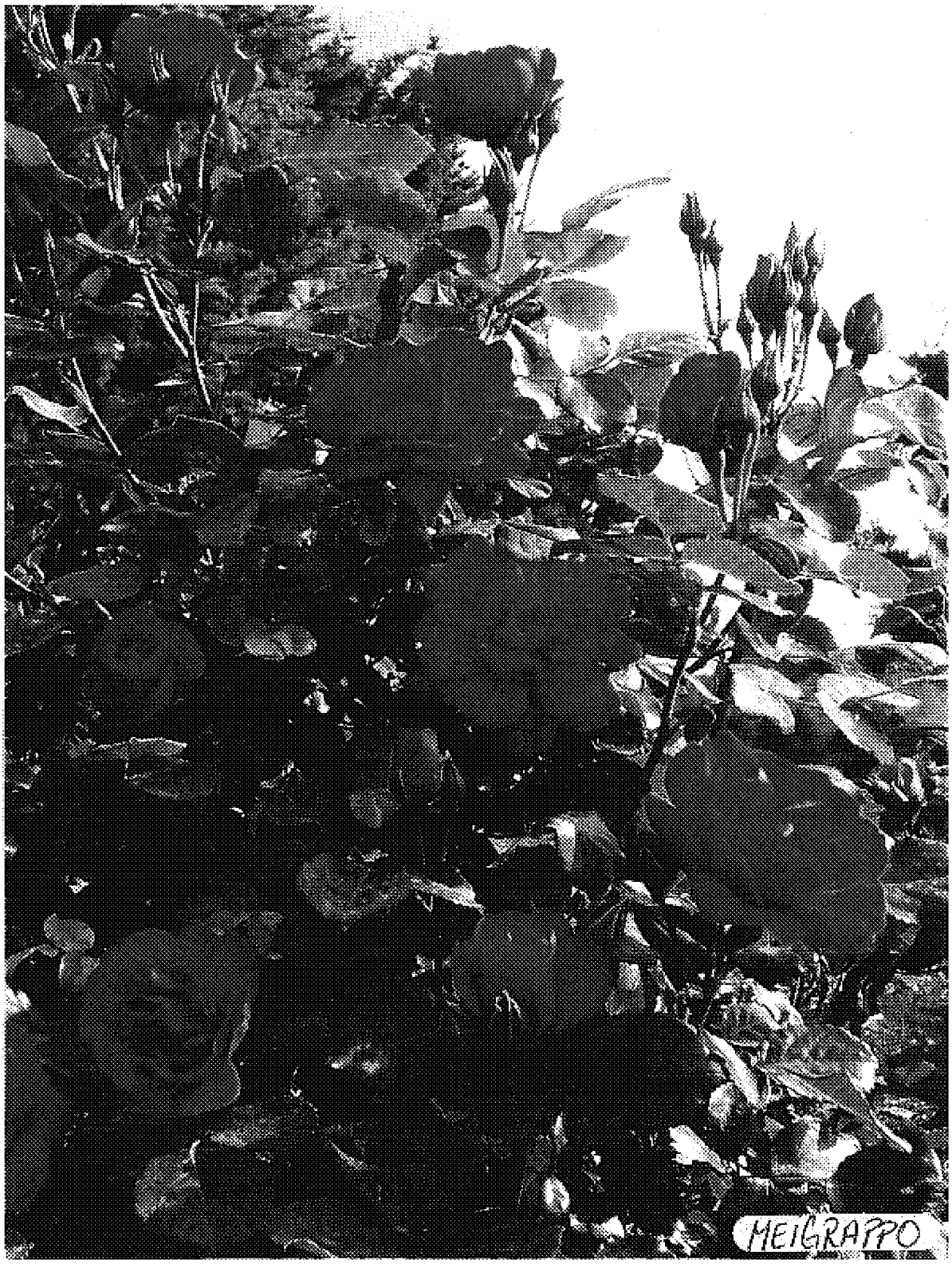

Botanical/commercial classification: *Rosa hybrida*/ Climbing Rose Plant.
Varietal denomination: cv. Meigrappo.

SUMMARY OF THE INVENTION

The new variety of climbing rose plant was created by artificial pollination wherein two parents were crossed which previously had been studied in the hope that they would contribute the desired characteristics. The female parent (i.e., the seed parent) of the new variety was the product of the cross of the 'Delsap' variety (non-patented in the United States) and the 'Meideuji' variety (non-patented in the United States). The male parent (i.e., the pollen parent) was the product of the cross of the 'Kortello' variety (non-patented in the United States) and the 'Delmur' variety (non-patented in the United States). The parentage of the new variety can be summarized as follows:

('Delsap'×'Meideuji')×('Kortello'×'Delmur').

The seeds resulting from the pollination were sown and small plants were obtained which were physically and biologically different from each other. Selective study resulted in the identification of a single plant of the new variety.

It was found that the new rose plant of the present invention displays the following combination of characteristics:

(a) exhibits a climbing growth habit, (b) abundantly forms on a nearly continuous basis attractive elegant blossoms that are red in coloration, (c) forms vigorous dense dark green semi-glossy foliage that contrasts well with the red blossom coloration, (d) displays good tolerance to Black Spot and Oidium, and (e) is well suited for providing attractive ornamentation in the landscape.

The new variety well meets the needs of the horticultural industry and can be grown to advantage in parks and gardens where attractive ornamentation is desired. It is particularly well suited for growing on a trellis, lamppost or gazebo.

The new variety of the present invention readily can be distinguished from its ancestors. For instance, the 'Delsap' variety commonly displays the inflorescence in clusters of approximately 20 to 30 flowers. The 'Meideuji' variety forms flowers having more petals and is sensitive to Black Spot. The 'Kortello' variety forms double blossoms having approximately 35 petals on average and displays a shrub growth habit. The 'Delmur' variety forms single flowers having approximately 7 petals on average.

The new variety of the present invention also can be readily distinguished from the 'Meidrason' variety (U.S. Plant Pat. No. 15,052) and the 'Meikousie' variety (non-patented in the United States) through an inspection of the flowers. More specifically, the 'Meidrason' flowers display a substantially greater number of petals, and the 'Meikousie' flowers display a dissimilar geranium coloration.

The new variety has been found to undergo asexual propagation at Le Cannet des Maures, Var, France, by a number of routes, including budding, grafting, and by the use of cuttings. Asexual propagation by the above-mentioned techniques at such location has shown that the characteristics of the new variety are firmly fixed and are stably transmitted by such asexual propagation from one generation to another. Accordingly, the new variety asexually reproduces in a true to type manner.

The new variety has been named 'Meigrappo'.

BRIEF DESCRIPTION OF THE PHOTOGRAPH

The accompanying photograph shows, as nearly true as it is reasonably possible to make the same in a color illustration of this character, a typical specimen of the new variety. The rose plant of the new variety was approximately two-and-a-half years of age and was photographed during November while growing outdoors on *Rosa froebelli* rootstock at Le Cannet des Maures, Var, France.

FIG. 1 illustrates the typical elegant flowers, buds in various stages of opening, and dark green semi-glossy foliage of the new variety.

DETAILED DESCRIPTION

The chart used in the identification of the colors is that of The Royal Horticultural Society (R.H.S. Colour Chart), London, England. The description is based on the observation of two-and-a-half-year-old plants during October while growing outdoors on *Rosa froebelli* rootstock at Le Cannet des Maures, Var, France.

Class: Climbing.

Plant:

*Height.*—Approximately 170 cm on average at the end of the growing season.

*Width.*—Approximately 150 cm on average at the end of the growing season.

*Habit.*—Climbing.

Branches:

*Thorns.*—Configuration: curved downwards on the upper surface, and concave on the under surface with an oval base. Size: commonly approximately 1 cm in length on average. Color: on young stems near Greyed-Orange Group 165B suffused with Red Group 46B, and on adult stems near Greyed-Orange Group 165B.

Leaves:

*General appearance.*—Very dense, dark green, and semi-glossy.

*Petioles.*—Upper surface: near Green Group 137C and slightly glandular. Under surface: near Green Group 137C, and commonly bear a few prickles. Length: commonly approximately 3.5 cm on average. Diameter: commonly approximately 2 mm on average.

*Stipules.*—General appearance: adnate, pectinate and rather broad.

*Size.*—A seven-leaflet leaf commonly is approximately 15.2 cm in length on average, and approximately 10.6 cm in width on average. Color: commonly near Green Group 137C on the upper surface and near Green Group 143B on the under surface.

*Leaflets.*—Number: 3, 5, and 7 (most often). Arrangement: alternate and odd pinnately compound. Size: a terminal leaflet commonly is approximately 6.1 cm in length on average and approximately 4.5 cm in width on average. Shape: generally oval (as illustrated). Apex: pointed and cuspidate. Base: obtuse. Margin: serrulate. Texture: somewhat leathery. Color (adult foliage): upper surface: near Yellow-Green Group 147A. Under surface: near Yellow-Green Group 147B.

Inflorescence:

*Number of flowers.*—Typically approximately 2 to 5 per stem.

*Peduncle.*—Bears some prickles, relatively firm in strength, approximately 3.5 cm in length, and near Green Group 138A in coloration.

*Sepals.*—Number: 5. Size: commonly approximately 3.2 cm in length on average and approximately 0.8 cm in width on average. Shape: with a long narrow point. Texture: tomentose on both surfaces. Color (upper surface): near Green Group 138B and 138C. Color (under surface): near Yellow-Green Group 144A.

*Buds.*—Shape: conical. Size: large. Length: Approximately 2 cm on average. Color: as the calyx breaks on the upper surface near Red Group 45A and amply suffused with velvety Red Group 46A, and on the under surface near Red Group 46A, and with a tiny spot of near Yellow Group 9A at the base.

*Flower.*—Shape: cup-shaped. Diameter: approximately 11 cm on average when fully open. Color (when opening): upper surface: near Red Group 45A and amply suffused with velvety Red Group 46A. Under surface: near Red Group 46A. basal spot: near Yellow Group 9A. Color (in course of opening): upper surface: near Red Group 45A and lightly suffused with Red Group 46A. Under surface: near Red Group 53B. basal spot: near Yellow Group 9D on the upper surface and absent on the under surface. Color (open blossom): upper surface: near Red Group 46B. lower surface: near Red Group 53B. basal spot: absent on upper and under surfaces. Fragrance: none. Petal number: commonly approximately 19 on average. Petal shape: obovate. Petal size: approximately 4.1 cm in length on average and approximately 3.6 cm in width on average. Petal arrangement: imbricated. Petal apex: reflected. Petaloids: none observed during observations to date. Lastingness: the blossoms commonly last approximately 10 to 15 days on the plant. Petal drop: very good with the petals detaching cleanly before drying. Receptacle: funnel-shaped and near Yellow-Green Group 144A in coloration. Hips: Generally near round, commonly approximately 1.9 cm in length, approximately 1.7 cm in width, and reddish in coloration.

Development:

*Vegetation.*—Very strong.

*Blooming.*—Very abundant, precocious, and nearly continuous.

*Aptitude to bear fruit.*—Good.

*Tolerance to diseases.*—Very good with respect to Black Spot and Oidium.

Plants of the 'Meigrappo' variety have not been observed under all possible environmental conditions to date. Accordingly, it is possible that the phenotypic expression may vary somewhat with changes in light intensity and duration, cultural practices, and other environmental conditions without variance in the genotype.

I claim:

1. A new and distinct Climbing Rose plant having the following combination of characteristics:

(a) exhibits a climbing growth habit, (b) abundantly forms on a nearly continuous basis attractive elegant blossoms that are red in coloration, (c) forms dense dark green semi-glossy foliage that contrasts well with the red blossom coloration, (d) displays good tolerance to Black Spot and Oidium, and (e) is well suited for providing attractive ornamentation in the landscape;

substantially as illustrated and described.

* * * * *